US006407126B1

(12) United States Patent
Schelberger et al.

(10) Patent No.: US 6,407,126 B1
(45) Date of Patent: Jun. 18, 2002

(54) FUNGICIDE MIXTURES BASED ON AMIDE COMPOUNDS AND PYRIDINE DERIVATIVES

(75) Inventors: Klaus Schelberger, Gönnheim; Maria Scherer, Landau; Karl Eicken, Wachenheim; Manfred Hampel, Neustadt; Eberhard Ammermann, Heppenheim; Gisela Lorenz, Neustadt; Siegfried Strathmann, Limburgerhof, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/581,905
(22) PCT Filed: Dec. 15, 1998
(86) PCT No.: PCT/EP98/08225
§ 371 (c)(1), (2), (4) Date: Jun. 19, 2000
(87) PCT Pub. No.: WO99/31951
PCT Pub. Date: Jul. 1, 1999

(30) Foreign Application Priority Data

Dec. 18, 1997 (DE) .......................... 197 56 378

(51) Int. Cl.⁷ ...................... A61K 31/44; C07D 213/04; A01M 43/40
(52) U.S. Cl. ........................ 514/355; 546/316; 504/116; 504/121; 504/124; 504/130
(58) Field of Search ................ 504/130, 124, 504/121, 116; 546/316; 514/355

(56) References Cited

U.S. PATENT DOCUMENTS 5,330,995 A    7/1994    Eicken

FOREIGN PATENT DOCUMENTS

| EP | 209 234 | 1/1987 |
| EP | 256 503 | 2/1988 |
| EP | 545 099 | 6/1993 |
| GB | 2 143 736 | 2/1985 |
| WO | 97/08952 | 3/1997 |
| WO | 97/10716 | 3/1997 |
| WO | 97/39628 | 10/1997 |

OTHER PUBLICATIONS

Derwent Abst. 83:23313.
Derwent Abst. 86:66780.
Derwent Abst. 97:105496.
Derwent Abst. 102:144694.
Derwent Abst. 88:70331.

Primary Examiner—Charandit S. Aulath
(74) Attorney, Agent, or Firm—Keil & Weinkauf

(57) ABSTRACT

Fungicidal mixtures comprise as active components
a) an amide compound of the formula I

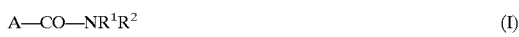

$$A-CO-NR^1R^2 \quad (I)$$

and at least one further ingredient selected from
b) a dithiocarbamate (II) selected from the group consisting of
manganese ethylenebis(dithiocarbamate) (zinc complex) (IIa),
manganese ethylenebis(dithiocarbamat) (IIb),
zinc ammoniate ethylenebis(dithiocarbamate) (IIc) and
zinc ethylenebis(dithiocarbamate) (IId)
c) a carbamate of the formula III

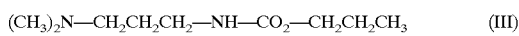

$$(CH_3)_2N-CH_2CH_2CH_2-NH-CO_2-CH_2CH_2CH_3 \quad (III)$$

d) an N-acetylbenzamide of the formula IV

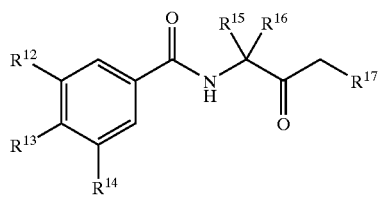

(IV)

or a salt or adduct thereof,
e) an active compound of the formula V,

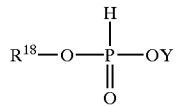

(V)

f) an active compound of the formula VI,

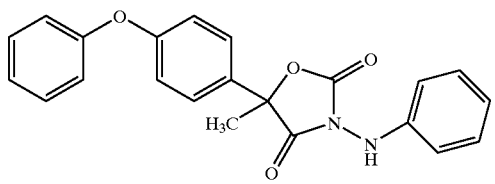

(VI)

and
g) an active compound of the formula VII,

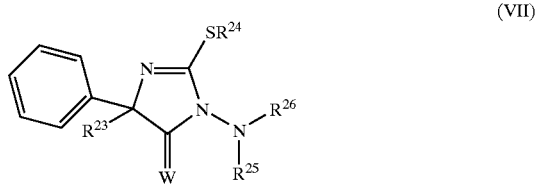

(VII)

where the substituents are as defined in the description, in a synergistically effective amount.

8 Claims, No Drawings

FUNGICIDE MIXTURES BASED ON AMIDE COMPOUNDS AND PYRIDINE DERIVATIVES

The present invention relates to fungicidal mixtures for controlling harmful fungi which comprise, in a synergistically effective amount, a) amide compounds of the formula I $$A-CO-NR^1R^2 \qquad \qquad I$$

in which

A is an aryl group or an aromatic or non-aromatic, 5- or 6-membered heterocycle which has from 1 to 3 hetero atoms selected from O, N and S;
  where the aryl group or the heterocycle may or may not have 1, 2 or 3 substituents which are selected, independently of one another, from alkyl, halogen, $CHF_2$, $CF_3$, alkoxy, haloalkoxy, alkylthio, alkylsulfynyl and alkylsulfonyl;

$R^1$ is a hydrogen atom;

$R^2$ is a phenyl or cycloalkyl group which may or may not have 1, 2 or 3 substituents which are selected from alkyl, alkenyl, alkynyl, alkoxy, alkenyloxy, alkynyloxy, cycloalkyl, cycloalkenyl, cycloalkyloxy, cycloalkenyloxy, phenyl and halogen, where the aliphatic and cycloaliphatic radicals may be partially or fully halogenated and/or the cycloaliphatic radicals may be substituted by from 1 to 3 alkyl groups and where the phenyl group may have from 1 to 5 halogen atoms and/or from 1 to 3 substituents which are selected, independently of one another, from alkyl, haloalkyl, alkoxy, haloalkoxy, alkylthio and haloalkylthio, and where the amidic phenyl group may be condensed with a saturated 5-membered ring which may or may not be substituted by one or more alkyl groups and/or may have a hetero atom selected from O and S, and b) a dithiocarbamate (II) selected from the group consisting of
  manganese ethylenebis(dithiocarbamate) (zinc complex) (IIa),
  manganese ethylenebis(dithiocarbamate) (IIb),
  zinc ammoniate ethylenebis(dithiocarbamate) (IIc) and
  zinc ethylenebis(dithiocarbamate) (IId)

and/or c) a carbamate of the formula III $$(CH_3)_2N-CH_2CH_2CH_2-NH-CO_2-CH_2CH_2CH_3 \qquad (III)$$

and/or d) an N-acetonylbenzamide of the formula IV (IV)

[Structure of formula IV with substituents $R^{12}$, $R^{13}$, $R^{14}$, $R^{15}$, $R^{16}$, $R^{17}$]

where the substituents have the following meaning:

e) an active ingredient of the formula V, (V)

$$R^{18}-O-\overset{H}{\underset{\overset{\|}{O}}{P}}-OY$$

where the substituents have the following meaning:
  $R^{12}$, $R^{14}$ independently of one another are halogen or $C_1-C_4$-alkyl;
  $R^{13}$ is cyano, $C_1-C_4$-alkyl, $C_2-C_4$-alkenyl, $C_2-C_4$-alkynyl or $C_1-C_4$-alkoxy;
  $R^{15}$ is hydrogen or $C_1-C_4$-alkyl;
  $R^{16}$ is $C_2-C_4$-alkyl;
  $R^{17}$ is thiocyanato, isothiocyanato or halogen, or a salt or adduct thereof, and/or b) [sic] an active ingredient of the formula V, (V)

$$R^{18}-\overset{H}{\underset{\overset{\|}{O}}{O}}-P-OY$$

where the substituents have the following meaning:
  Y is hydrogen, a metal atom of the first to the third main group of the Periodic Table of the Elements or a group $NR^{19}R^{20}R^{21}R^{22}$;
  $R^{18}$ is hydrogen, a $C_1-C_{18}$-alkyl group which may be substituted by halogen or a nitro group, a $C_2-C_8$-alkenyl or $C_2-C_8$-alkynyl group which may be substituted by halogen or a nitro group, a $C_1-C_8$-alkoxy-$C_1-C_8$-alkyl or a $C_2-C_8$-alkenyl-$C_1-C_8$-alkyl group, an unsubstituted or substituted aryl group having 6 to 14 carbon atoms, a $C_3-C_7$-cycloalkyl group, a $C_1-C_4$-alkylaryl group or a heterocyclic group having 5 or 6 ring atoms and a hetero atom selected from the group consisting of N, O or S, where the heterocyclic group is attached directly or via an aliphatic chain to the oxygen atom, and
  $R^{19}-R^{22}$ independently of one another are a $C_1-C_4$-alkyl group or a $C_1-C_4$-hydroxyalkyl group, and/or f) an active ingredient of the formula VI, (VI)

[Structure of formula VI]

and/or g) an active ingredient of the formula VII,

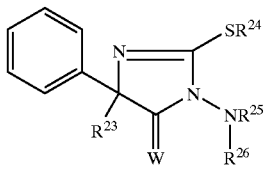

(VII)

where the substituents $R^{23}$ to $R^{26}$ have the following meanings:

H, $C_1$–$C_6$-alkyl, $C_1$–$C_6$-haloalkyl, $C_2$–$C_6$-alkenyl, $C_2$–$C_6$-alkynyl, $C_1$–$C_4$-alkoxycarbonyl, $C_1$–$C_4$-alkylcarbonyl, formyl, $C_3$–$C_7$-cycloalkyl, $C_6$–$C_{10}$-aryl, unsubstituted or $C_1$–$C_4$-alkyl-, $C_1$–$C_4$-alkoxy-, nitro- or halogen-substituted, $C_1$–$C_6$-alkoxy, $C_2$–$C_6$-alkoxyalkyl, $C_2$–$C_6$-alkylthioalkyl, di-$C_1$–$C_4$-alkylaminoalkyl, pyridyl, thiazolyl, furyl or thienyl and W is O, S or S=O.

The amide compounds of the formula I are known per se and described in the literature (EP-A 545 099).

WO 97/08952 describes fungicidal mixtures which, in addition to compounds of the formula I, contain fenazaquin as further components. These mixtures are described as being very effective against Botrytis.

Also known are the dithiocarbamates II (IIa: common name: mancozeb, U.S. Pat. No. 3,379,610; IIb: common name: maneb, U.S. Pat. No. 2,504,404; IIc: former common name: metiram, U.S. Pat. No. 3,248,400; IId: common name: zineb, U.S. Pat. No. 2,457,674), their preparation and their action against harmful fungi.

Also known is the compound III, its preparation and its use (German Laid-Open Application DOS 15 67 169, common name: propamocarb).

Synergistic mixtures of the compounds IV with dithiocarbamates, their preparation and their action against harmful fungi are known from EP-A 753 258 and U.S. Pat. No. 5,304,572.

The compounds V are described in the literature as fungicides and insecticides (for example DE 24 63 046 and the literature cited therein. A known representative of this class of active ingredients is commercially available under the common name fosetyl or fosetyl-Al.

The compound VI is known under the proposed common name famoxa-done (Proc. Brighton Crop Protection Conference 1996, Pests and Diseases, pages 21–26).

Compounds of the formula VII are known, inter alia, from EP-A 551,048 and EP-A 629,616.

It is an object of the present invention to provide mixtures which have an improved activity against harmful fungi combined with a reduced total amount of active ingredients applied (syner-gistic mixtures), with a view to reducing the application rates and to improving the activity spectrum of the known compounds.

We have found that this object is achieved by the mixtures defined at the outset. Moreover, we have found that better control of harmful fungi is possible by applying the compounds I and the compounds II to V simultaneously, that is either together or separately, or by applying the compounds I and the compounds II to V in succession than when the compounds I or II to V are applied on their own.

The mixtures according to the invention have synergistic action and are therefore particularly suitable for controlling harmful fungi and in particular mildew on grapevines.

In the context of the present invention, halogen is fluorine, chlorine, bromine and iodine and is in particular fluorine, chlorine and bromine.

The term "alkyl" includes straight-chain and branched alkyl groups. These are preferably straight-chain or branched $C_1$–$C_{12}$-alkyl and in particular $C_1$–$C_6$-alkyl groups. Examples of alkyl groups are alkyl such as, in particular, methyl, ethyl, propyl, 1-methylethyl, butyl, 1-methylpropyl, 2-methylpropyl, 1,1-di-methylethyl, n-pentyl, 1-methylbutyl, 2-methylbutyl, 3-methyl-butyl, 1,2-dimethylpropyl, 1,1-dimethylpropyl, 2,2-dimethyl-propyl, 1-ethylpropyl, n-hexyl, 1-methylpentyl, 2-methylpentyl, 3-methylpentyl, 4-methylpentyl, 1,2-dimethylbutyl, 1,3-dimethyl-butyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 1-methylhexyl, 1-ethylpentyl, 2-ethylpentyl, 1-propylbutyl, octyl, decyl, dodecyl.

Haloalkyl is an alkyl group as defined above which is partially or fully halogenated by one or more halogen atoms, in particular by fluorine and chlorine. Preferably, there are from 1 to 3 halogen atoms present, and the difluoromethyl or the trifluoromethyl group is particularly preferred.

The above statements for the alkyl group and the haloalkyl group apply in a corresponding manner to the alkyl and haloalkyl group in alkoxy, haloalkoxy, alkylthio, haloalkylthio, alkylsulfynyl and alkylsulfonyl.

The alkenyl group includes straight-chain and branched alkenyl groups. These are preferably straight-chain or branched $C_3$–$C_{12}$-alkenyl groups and in particular $C_3$–$C_6$-alkenyl groups. Examples of alkenyl groups are 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,1-dimethyl-3-butenyl [sic], 1,2-di-methyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-l-methyl-2-propenyl and 1-ethyl-2-methyl-2-propenyl, in particular 2-propenyl, 2-butenyl, 3-methyl-2-butenyl and 3-methyl-2-pentenyl.

The alkenyl group may be partially or fully halogenated by one or more halogen atoms, in particular by fluorine or chlorine. The alkenyl group preferably has from 1 to 3 halogen atoms.

The alkynyl group includes straight-chain and branched alkynyl groups. These are preferably straight-chain and branched $C_3$–$C_{12}$-alkynyl groups and in particular $C_3$–$C_6$-alkynyl groups. Examples of alkynyl groups are 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-alkynyl [sic], 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,2-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl.

The above statements for the alkenyl group and its halogen substituents and for the alkynyl group apply in a corresponding manner to alkenyloxy and alkynyloxy.

The cycloalkyl group is preferably a $C_3$–$C_6$-cycloalkyl group, such as cyclopropyl, cyclobutyl, cyclopentyl or cyclohexyl. If the cycloalkyl group is substituted, it preferably has from 1 to 3 $C_1$–$C_4$-alkyl radicals as substituents.

Cycloalkenyl is preferably a $C_4$–$C_6$-cycloalkenyl group, such as cyclobutenyl, cyclopentenyl or cyclohexenyl. If the cycloalkenyl group is substituted, it preferably has from 1 to 3 $C_1$–$C_4$-alkyl radicals as substituents.

A cycloalkoxy group is preferably a $C_5$–$C_6$-cycloalkoxy group, such as cyclopentyloxy or cyclohexyloxy. If the cycloalkoxy group is substituted, it preferably has from 1 to 3 $C_1$–$C_4$-alkyl radicals as substituents.

The cycloalkenyloxy group is preferably a $C_5$–$C_6$-cycloalkenyloxy group, such as cyclopentyloxy or cyclohexyloxy. If the cycloalkenyloxy group is substituted, it preferably has from 1 to 3 $C_1$–$C_4$-alkyl radicals as substituents.

Aryl is preferably phenyl.

If A is a phenyl group, this may have one, two or three of the abovementioned substituents in any position. These substituents are preferably selected, independently of one another, from alkyl, difluoromethyl, trifluoromethyl and halogen, in particular chlorine, bromine and iodine. Particularly preferably, the phenyl group has a substituent in the 2-position.

If A is a 5-membered heterocycle, it is in particular a furyl, thiazolyl, pyrazolyl, imidazolyl, oxazolyl, thienyl, triazolyl or thiadiazolyl radical or the corresponding dihydro or tetrahydro derivatives thereof. Preference is given to a thiazolyl or pyrazolyl radical.

If A is a 6-membered heterocycle, it is in particular a pyridyl radical or a radical of the formula:

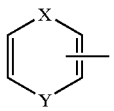

in which one of the radicals X and Y is O, S or $NR^{23}$, where $R^{23}$ is H or alkyl, and the other of the radicals X and Y is $CH_2$, S, SO, $SO_2$ or $NR^{23}$. The dotted line means that a double bond may or may not be present.

The 6-membered aromatic heterocycle is particularly preferably a pyridyl radical, in particular a 3-pyridyl radical, or a radical of the formula (A3)

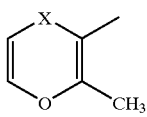

in which X is $CH_2$, S, SO or $SO_2$.

The abovementioned heterocyclic radicals may or may not have 1, 2 or 3 of the abovementioned substituents, where these substituents are preferably selected, independently of one another, from alkyl, halogen, difluoromethyl or trifluoromethyl.

A is particularly preferably a radical of the formulae:

(A1)

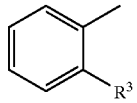

(A2)

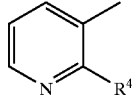

(A5)

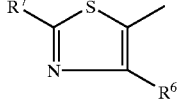

(A7)

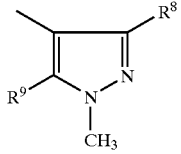

in which $R^3$, $R^4$, $R^6$, $R^7$, $R^8$ and $R^9$ independently of one another are hydrogen, alkyl, in particular methyl, halogen, in particular chlorine, $CHF_2$ or $CF_3$.

The radical $R^1$ in the formula I is preferably a hydrogen atom.

The radical $R^2$ in the formula I is preferably a phenyl radical. $R^2$ preferably has at least one substituent which is particularly preferably present in the 2-position. The substituent (or the substituents) is (are) preferably selected from the group consisting of alkyl, cycloalkyl, cycloalkenyl, halogen or phenyl.

The substituents of the radical $R^2$ may in turn be substituted again. The aliphatic or cycloaliphatic substituents may be partially or fully halogenated, in particular fluorinated or chlorinated. They preferably have 1, 2 or 3 fluorine or chlorine atoms. If the substituent of the radical $R^2$ is a phenyl group, this phenyl group may preferably be substituted by from 1 to 3 halogen atoms, in particular chlorine atoms, and/or by a radical which is preferably selected from alkyl and alkoxy. Particularly preferably, the phenyl group is substituted with a halogen atom in the p-position, i.e. the particularly preferred substituent of the radical $R^2$ is a p-halogen-substituted phenyl radical. The radical $R^2$ may also be condensed with a saturated 5-membered ring, where this ring for its part may have from 1 to 3 alkyl substituents.

$R^2$ is in this case, for example, indanyl, thiaindanyl and oxaindanyl. Preference is given to indanyl and 2-oxaindanyl which are attached to the nitrogen atom, in particular via the 4-position.

According to a preferred embodiment, the composition according to the invention comprises as amide compound a compound of the formula I in which A has the following meanings:

phenyl, pyridyl, dihydropyranyl, dihydrooxathiynyl, dihydrooxathiynyloxide, dihydrooxathiynyldioxide, furyl, thiazolyl, pyrazolyl or oxazolyl, where these groups may have 1, 2 or 3 substituents which are selected, independently of one another, from alkyl, halogen, difluoromethyl and trifluoromethyl.

According to a further preferred embodiment, A is:

pyridin-3-yl, which may or may not be substituted in the 2-position by halogen, methyl, difluoromethyl, trifluoromethyl, methoxy, methylthio, methylsulfynyl or methylsulfonyl; phenyl, which may or may not be substituted in the 2-position by methyl, trifluoromethyl, chlorine, bromine or iodine;

2-methyl-5,6-dihydropyran-3-yl;

2-methyl-5,6-dihydro-1,4-oxathiyn-3-yl or the 4-oxide or 4,4-dioxide thereof;

2-methylfuran-3-yl, which may or may not be substituted in the 4- and/or 5-position by methyl;

thiazol-5-yl, which may or may not be substituted in the 2- and/or 4-position by methyl, chlorine, difluoromethyl or trifluoromethyl;

thiazol-4-yl, which may or may not be substituted in the 2- and/or 5-position by methyl, chlorine, difluoromethyl or trifluoromethyl;

1-methylpyrazol-4-yl, which may or may not be substituted in the 3- and/or 5-position by methyl, chlorine, difluoromethyl or trifluoromethyl; or oxazol-5-yl, which may or may not be substituted in the 2- and/or 4-position by methyl or chlorine.

According to a further preferred embodiment, the compositions according to the invention comprise as amide compound a compound of the formula I in which $R^2$ is a phenyl group which may or may not be substituted by 1, 2 or 3 of the abovementioned substituents.

According to a further preferred embodiment, the compositions according to the invention comprise as amide compound a compound of the formula I in which $R^2$ is a phenyl group which has one of the following substituents in the 2-position:

$C_3$–$C_6$-alkyl, $C_5$–$C_6$-cycloalkenyl, $C_5$–$C_6$-cycloalkyloxy, cycloalkenyloxy, where these groups may be substituted by 1, 2 or 3 $C_1$–$C_4$-alkyl groups, phenyl, which is substituted by from 1 to 5 halogen atoms and/or from 1 to 3 groups which are selected, independently of one another, from $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-haloalkylthio, indanyl or oxaindanyl which may or may not be substituted by 1, 2 or 3 $C_1$–$C_4$-alkyl groups.

According to a further preferred embodiment, the compositions according to the invention comprise as amide compound a compound of the formula Ia,

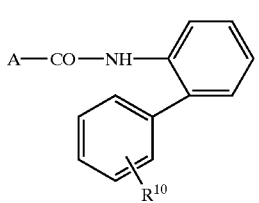

(Ia)

in which

A is

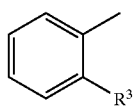

(A1)

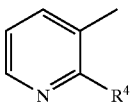

(A2)

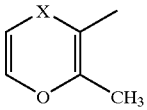

(A3)

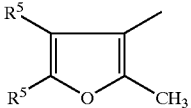

(A4)

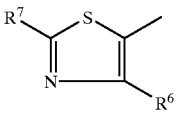

(A5)

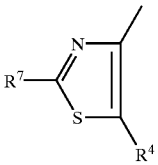

(A6)

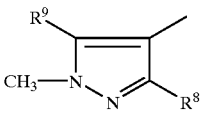

(A7)

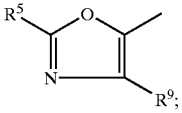

(A8)

X is methylene, sulfur, sulfynyl or sulfonyl ($SO_2$), $R^3$ is methyl, difluoromethyl, trifluoromethyl, chlorine, bromine or iodine, $R^4$ is trifluoromethyl or chlorine, $R^5$ is hydrogen or methyl, $R^6$ is methyl, difluoromethyl, trifluoromethyl or chlorine, $R^7$ is hydrogen, methyl or chlorine, $R^8$ is methyl, difluoromethyl or trifluoromethyl, $R^9$ is hydrogen, methyl, difluoromethyl, trifluoromethyl or chlorine, $R^{10}$ is $C_1$–$C_4$-alkyl, $C_1$–$C_4$-alkoxy, $C_1$–$C_4$-alkylthio or halogen.

According to a particularly preferred embodiment, the compositions comprise as amide compound a compound of the formula Ib

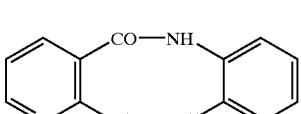

(Ib)

in which $R^4$ is halogen and $R^{11}$ is phenyl which is substituted by halogen.

Useful amide compounds of the formula I are mentioned in EP-A-545 099 and 589 301 which are incorporated herein in their entirety by reference.

The preparation of the amide compounds of the formula I is known, for example, from EP-A-545 099 or 589 301 or can be carried out by similar processes.

The formula IV represents in particular N-acetonylbenzamides in which the combination of the substituents corresponds to one row of the following table:

$$\text{(IV)}$$

[Structure: benzamide with $R^{12}$, $R^{13}$, $R^{14}$ on ring, C(=O)–NH–C($R^{15}$)($R^{16}$)–C(=O)–$R^{17}$]

| No.  | $R^1$ | $R^2$    | $R^3$ | $R^4$      | $R^5$  | $R^6$ |
|------|-------|----------|-------|------------|--------|-------|
| IV.1 | Cl    | $CH_3$   | Cl    | $CH_2CH_3$ | $CH_3$ | Cl    |
| IV.2 | Cl    | $CH_2CH_3$ | Cl  | $CH_2CH_3$ | $CH_3$ | Cl    |
| IV.3 | Cl    | $OCH_3$  | Cl    | $CH_2CH_3$ | $CH_3$ | Cl    |
| IV.4 | Cl    | $OCH_2CH_3$ | Cl | $CH_2CH_3$ | $CH_3$ | Cl    |
| IV.5 | Cl    | CN       | Cl    | $CH_2CH_3$ | $CH_3$ | Cl    |
| IV.6 | Br    | $CH_3$   | Br    | $CH_2CH_3$ | $CH_3$ | Cl    |
| IV.7 | Br    | CN       | Br    | $CH_2CH_3$ | $CH_3$ | Cl    |

Particular preference is given to the generally preferred and particularly preferred N-acetonylbenzamides in EP-A 753 258.

The formula V in particular represents compounds in which $R^{18}$ is hydrogen or a $C_1$–$C_4$-alkyl group, in particular an ethyl group (—$CH_2CH_3$), and Y is a metal of group III of the Periodic Table of the Elements. Metals of the first and the second subgroup, such as Li, K, Na, Cs, Mg or Ca, to name but a few examples, are also suitable.

In principle, however, the compounds V in which $R^{18}$ and $R^{19}$–$R^{22}$ are as defined at the outset are also suitable.

A particularly preferred compound V is the active ingredient known under the name fosetyl, or its Al salt fosetyl-Al.

The compound of the formula VI (proposed common name: famoxa-done), its preparation and its fungicidal properties are described in Proc. Brighton Crop Prot. Conference 1996, pages 21 to 26.

The compounds of the formula VII and their preparation are described, for example, in EP-A 551,048, EP-A 629,616 and EP-A 668,270. Preferred compounds of the formula VII are those which are described in the tables on pages 10, 11, 13, 14, 15 (for B=NH), 18 and 19 of EP-A 551,048.

Particularly preferred compounds VII are those in which $R^{23}$ is $C_1$–$C_6$-alkyl (in particular methyl, ethyl or propyl), $C_1$–$C_6$-haloalkyl or phenyl, $R^{24}$ is $C_1$–$C_6$-alkyl (preferably methyl), $C_1$–$C_6$-alkylthio (preferably methylthio), $R^{25}$ is phenyl, unsubstituted or substituted by $C_1$–$C_4$-alkyl, halogen, nitro, $C_1$–$C_4$-alkoxy, $C_1$–$C_4$-alkylcarbonyl, pyridyl, furyl, thienyl, thiazolyl, thienyl or naphthyl, unsubstituted or substituted by $C_1$–$C_4$-alkyl, and $R^{26}$ is hydrogen or $C_1$–$C_6$-alkyl.

To unfold the synergistic activity, even a small amount of the amide compound of the formula I is sufficient. Preference is given to employing amide compound and active ingredient of the formula II and/or III to V in a weight ratio in the range of from 50:1 to 1:50, in particular from 10:1 to 1:10. It is also possible here to employ ternary mixtures or mixtures having more than three active components which, in addition to amide compounds I, comprise both compounds II and compounds III, IV and/or V. In such mixtures, the mixing ratio of the compounds II, III, IV and V with each other is usually in the range of from 50:1 to 1:50, preferably from 10:1 to 1:10.

Owing to the basic character of their nitrogen atoms, the compounds IV are capable of forming salts or adducts with inorganic or organic acids or with metal ions.

Examples of inorganic acids are hydrohalic acids such as hydrofluoric acid, hydrochloric acid, hydrobromic acid and hydriodic acid, sulfuric acid, phosphoric acid and nitric acid.

Suitable organic acids are, for example, formic acid and alkanoic acids, such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulfonic acids (sulfonic acids having straight-chain or branched alkyl radicals of 1 to 20 carbon atoms), arylsulfonic acids or aryldisulfonic acids (aromatic radicals, such as phenyl and naphthyl, which carry one or two sulfo groups), alkylphosphonic acids (phosphonic acids having straight-chain or branched alkyl radicals of 1 to 20 carbon atoms), arylphosphonic acids or aryldiphosphonic acids (aromatic radicals, such as phenyl and naphthyl, which carry one or two phosphonic acid radicals), it being possible for the alkyl or aryl radicals to carry further substituents, e.g. p-toluenesulfonic acid, salicylic acid, p-aminosalicylic acid, 2-phenoxybenzoic acid, 2-acetoxybenzoic acid, etc.

Suitable metal ions are, in particular, the ions of the elements of the first to eighth subgroup, in particular chromium, manganese, iron, cobalt, nickel, copper, zinc and furthermore of the second main group, in particular calcium and magnesium, and of the third and fourth main group, in particular aluminum, tin and lead. The metals can exist in the various valencies which they can assume.

When preparing the mixtures, it is preferred to employ the pure active ingredients I and II to V, to which further active ingredients against harmful fungi or other pests, such as insects, arachnids or nematodes, or else herbicidal or growth-regulating active ingredients or fertilizers can be admixed.

The mixtures of the compounds I and II and/or III and/or IV and/or V, or the compounds I and II and/or III and/or IV and/or V used simultaneously, jointly or separately, exhibit outstanding activity against a wide range of phytopathogenic fungi, in particular from the classes of the Ascomycetes, Basidiomycetes, Phycomycetes and Deuteromycetes. Some of them act systemically and can therefore be employed as foliar- and soil-acting fungicides.

They are especially important for controlling a large number of fungi in a variety of crop plants, such as cotton, vegetable species (e.g. cucumbers, beans, tomatoes, potatoes and cucurbits), barley, grass, oats, bananas, coffee, maize, fruit species, rice, rye, soya, grapevine, wheat, ornamentals, sugar cane, and a variety of seeds.

They are particularly suitable for controlling the following phytopathogenic fungi: *Erysiphe graminis* (powdery mildew) in cereals, *Erysiphe cichoracearum* and *Sphaerotheca fuliginea* in cucurbits, *Podosphaera leucotricha* in apples, *Uncinula necator* in grapevines, Puccinia species in cereals, Rhizoctonia species in cotton, rice and lawns, Ustilago species in cereals and sugar cane, *Venturia inaequalis* (scab) in apples, Helminthosporium species in cereals, *Septoria nodorum* in wheat, *Botrytis cinerea* (gray mold) in strawberries, vegetables, ornamentals and grapevines, *Cercospora arachidicola* in groundnuts, *Pseudocercosporella herpotrichoides* in wheat and barley, *Pyricularia oryzae* in rice, *Phytophthora infestans* in potatoes and tomatoes, *Plasmopara viticola* in grapevines, Pseudoperonospora species in hops and cucumbers, Alternaria species in vegetables and fruit, Mycosphaerella species in bananas and Fusarium and Verticillium species.

Particularly preferably, the mixtures according to the invention can be used for controlling mildew in crops of cereals and grapevines.

The compounds II and/or III to VII can be applied simultaneously, either jointly or separately, or in succession, the sequence, in the case of separate application, generally not having any effect on the result of the control measures.

Depending on the kind of effect desired, the application rates of the mixtures according to the invention are, in particular in agricultural crop areas, from 0.01 to 8 kg/ha, preferably 0.1 to 5 kg/ha, in particular 0.5 to 3.0 kg/ha.

The application rates of the compounds I are from 0.01 to 2.5 kg/ha, preferably 0.05 to 2.5 kg/ha, in particular 0.1 to 1.0 kg/ha.

Correspondingly, in the case of the compounds II and/or III and/or IV and/or V and/or VI and/or VII, the application rates are from 0.01 to 10 kg/ha, preferably 0.05 to 5 kg/ha, in particular 0.05 to 2.0 kg/ha.

For seed treatment, the application rates of the mixture are generally from 0.001 to 250 g/kg of seed, preferably 0.01 to 100 g/kg, in particular 0.01 to 50 g/kg.

If phytopathogenic harmful fungi are to be controlled, the separate or joint application of the compounds I and II and/or III and/or IV and/or V and/or VI and/or VII or of the mixtures of the compounds I and II and/or III and/or IV and/or V and/or VI and/or VII is effected by spraying or dusting the seeds, the plants or the soils before or after sowing of the plants, or before or after plant emergence.

The fungicidal synergistic mixtures according to the invention, or the compounds I and II and/or III and/or IV and/or V and/or VI and/or VII, can be formulated for example in the form of ready-to-spray solutions, powders and suspensions or in the form of highly concentrated aqueous oily or other suspensions, dispersions, emulsions, oil dispersions, pastes, dusts, materials for broadcasting or granules, and applied by spraying, atomizing, dusting, broadcasting or watering. The use form depends on the intended purpose; in any case, it should ensure as fine and uniform a distribution as possible of the mixture according to the invention.

The formulations are prepared in a known manner, e.g. by extending the active ingredient with solvents and/or carriers, if desired using emulsifiers and dispersants, it being possible also to use other organic solvents as auxiliary solvents if water is used as the diluent. Suitable auxiliaries for this purpose are essentially: solvents such as aromatics (e.g. xylene), chlorinated aromatics (e.g. chlorobenzenes), paraffins (e.g. mineral oil fractions), alcohols (e.g. methanol, butanol), ketones (e.g. cyclohexanone), amines (e.g. ethanolamine, dimethylformamide) and water; carriers such as ground natural minerals (e.g. kaolins, clays, talc, chalk) and ground synthetic minerals (e.g. finely divided silica, silicates); emulsifiers such as nonionic and anionic emulsifiers (e.g. polyoxyethylene fatty alcohol ethers, alkylsulfonates and arylsulfonates) and dispersants such as lignosulfite waste liquors and methylcellulose.

Suitable surfactants are the alkali metal salts, alkaline earth metal salts and ammonium salts of aromatic sulfonic acids, e.g. ligno-, phenol-, naphthalene- and dibutylnaphthalenesulfonic acid, and of fatty acids, alkyl- and alkylarylsulfonates, alkyl, lauryl ether and fatty alcohol sulfates, and salts of sulfated hexa-, hepta- and octadecanols, or of fatty alcohol glycol ethers, condensates of sulfonated naphthalene and its derivatives with formaldehyde, condensates of naphthalene or of the naphthalenesulfonic acids with phenol and formaldehyde, polyoxyethylene A octylphenol ether, ethoxylated isooctyl-, octyl- or nonylphenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors or methylcellulose.

Powders, materials for broadcasting and dusts can be prepared by mixing or jointly grinding the compounds I or II and/or III and/or IV and/or V and/or VI and/or VII, or the mixture of the compounds I and II and/or III and/or IV and/or V and/or VI and/or VII, with a solid carrier.

Granules (e.g. coated granules, impregnated granules or homogeneous granules) are usually prepared by binding the active ingredient, or active ingredients, to a solid carrier.

Fillers or solid carriers are, for example, mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials and fertilizers, such as ammonium sulfate, ammonium phosphate, ammonium nitrate, ureas, and products of vegetable origin, such as cereal meal, tree bark meal, wood meal and nutshell meal, cellulose powders or other solid carriers.

The formulations generally comprise from 0.1 to 95% by weight, preferably 0.5 to 90% by weight, of one of the compounds I or II and/or III and/or IV and/or V and/or VI and/or VII or of the mixture of the compounds I and II and/or III and/or IV and/or V and/or VI and/or VII. The active ingredients are employed in a purity of from 90% to 100%, preferably 95% to 100% (according to NMR spectrum or HPLC).

The compounds I and II and/or III and/or IV and/or V and/or VI and/or VII, the mixtures, or the corresponding formulations, are applied by treating the harmful fungi, their habitat, or the plants, seeds, soils, areas, materials or spaces to be kept free from them with a fungicidally effective amount of the mixture, or of the compounds I and II and/or III and/or IV and/or V and/or VI. and/or VII in the case of separate application.

Application may be carried out before or after infection by the harmful fungi.

Examples of such preparations comprising the active ingredients are:

I. A solution of 90 parts by weight of the active ingredients and 10 parts by weight of N-methylpyrrolidone; this solution is suitable for use in the form of microdrops;

II. A mixture of 20 parts by weight of the active ingredients, 80 parts by weight of xylene, 10 parts by weight of the adduct of 8 to 10 mol of ethylene oxide to 1 mol of oleic acid N-monoethanolamide, 5 parts by weight of the calcium salt of dodecylbenzenesulfonate, 5 parts by weight of the adduct of 40 mol of ethylene oxide to 1 mol of castor oil; a dispersion is obtained by finely distributing the solution in water;

III. An aqueous dispersion of 20 parts by weight of the active ingredients, 40 parts by weight of cyclohexanone, 30 parts by weight of isobutanol, 20 parts by weight of the adduct of 40 mol of ethylene oxide to 1 mol of castor oil;

IV. An aqueous dispersion of 20 parts by weight of the active ingredients, 25 parts by weight of cyclohexanol, 65 parts by weight of a mineral oil fraction of boiling point 210 to 280° C., and 10 parts by weight of the adduct of 40 mol of ethylene oxide to 1 mol of castor oil;

V. A mixture, ground in a hammer mill, of 80 parts by weight of the active ingredients, 3 parts by weight of the sodium salt of diisobutylnaphthalene-1-sulfonate, 10 parts by weight of the sodium salt of a lignosulfonic acid from a sulfite waste liquor and 7 parts by weight of pulverulent silica gel; a spray mixture is obtained by finely distributing the mixture in water;

VI. An intimate mixture of 3 parts by weight of the active ingredients and 97 parts by weight of finely divided kaolin; this dust comprises 3% by weight of active ingredient;

VII. An intimate mixture of 30 parts by weight of the active ingredients, 92 parts by weight of pulverulent silica gel and 8 parts by weight of paraffin oil which had been sprayed onto the surface of this silica gel; this formulation imparts good adhesion to the active ingredient;

VIII. A stable aqueous dispersion of 40 parts by weight of the active ingredients, 10 parts by weight of the sodium salt of a phenolsulfonic acid/urea/formaldehyde condensate, 2 parts by weight of silica gel and 48 parts by weight of water; this dispersion may be diluted further;

IX. A stable oily dispersion of 20 parts by weight of the active ingredients, 2 parts by weight of the calcium salt of dodecylbenzenesulfonate, 8 parts by weight of fatty alcohol polyglycol ether, 20 parts by weight of the sodium salt of a phenolsulfonic acid/urea/formaldehyde condensate and 88 parts by weight of a paraffinic mineral oil.

USE EXAMPLE

The synergistic activity of the mixtures according to the invention can be demonstrated by the following experiments:

The active ingredients, separately or jointly, are formulated as a 10% emulsion in a mixture of 63% by weight of cyclohexanone and 27% by weight of emulsifier, and diluted with water to the desired concentration.

Evaluation is carried out by determining the infected leaf areas in percent. These percentages are converted into efficacies. The efficacy (W) is calculated as follows using Abbot's formula:

$$W=(1-\alpha)\cdot 100/\beta$$

α corresponds to the fungal infection of the treated plants in % and

β corresponds to the fungal infection of the untreated (control) plants in %

An efficacy of 0 means that the infection level of the treated plants corresponds to that of the untreated control plants; an efficacy of 100 means that the treated plants were not infected.

The expected efficacies of the mixtures of the active ingredients were determined using Colby's formula [R. S. Colby, Weeds 15, 20–22 (1967)] and compared with the observed efficacies.

Colby's formula: $E = x + y - x \cdot y / 100$

E expected efficacy, expressed in % of the untreated control, when using the mixture of the active ingredients A and B at the concentrations a and b x efficacy, expressed in % of the untreated control, when using active ingredient A at a concentration of a y efficacy, expressed in % of the untreated control, when using active ingredient B at a concentration of b

Use Example 1

Activity Against Phytophthora Infestans on Tomatoes

Leaves of potted plants of variety "Große Fleischtomate" were sprayed to runoff point with an aqueous suspension which had been prepared from a stock solution comprising 10% of active compound, 63% of cyclohexanone and 27% of emulsifier. The next day, the leves were infected with an aqueous zoospore suspension of Phytophthora infestans. The plants were subsequently placed in a chamber saturated with water vapor, at temperatures between 16 and 18° C. After 6 days, the tomato blight on the untreated but infected control plants had developed to such an extent that the infection could be determined visually in %.

The compounds of the formula I employed were the following components:

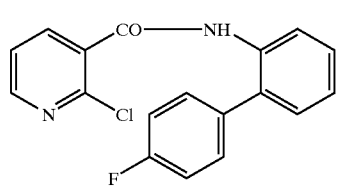

I.1

The results are shown in Tables 1 and 2 below.

TABLE 1

| Ex. | Active ingredient | Concentration of active ingredient in the spray liquor in ppm | Efficacy in % of the untreated control |
|---|---|---|---|
| 1C | Control (untreated) | 0 (99% infection) | 0 |
| 2C | Compound I.1 | 100 | 0 |
|  |  | 50 | 0 |
| 4C | Compound IIa | 12.5 | 70 |
| 5C | Compound VI | 100 | 80 |
|  |  | 50 | 70 |
|  |  | 25 | 70 |

TABLE 2

| Ex | Mixtures according to the invention (content in ppm) | Observed efficacy | Calculated efficacy *) |
|---|---|---|---|
| 7 | 100 ppm I.1 + 100 ppm VI | 95 | 80 |
| 8 | 50 ppm I.1 + 50 ppm VI | 85 | 70 |

*) calculated using Colby's formula

The test results show that the observed efficacy in all mixing ratios is higher than the efficacy which had been calculated beforehand using Colby's formula.

We claim:

1. A fungicidal composition comprising as active components a) an amide compound of formula Ia

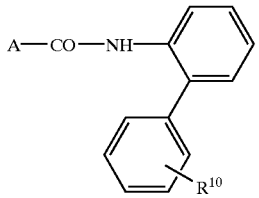

in which
A is a radical

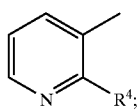

$R^4$ is trifluoromethyl or chlorine, and
$R^{10}$ is $C_1$–$C_4$-alkyl, $C_1$–$C_4$-alkoxy, $C_1$–$C_4$-alkylthio or halogen; and at least one further active ingredient selected from the group consisting of:

b) a dithiocarbamate (II) selected from the group consisting of
  manganese ethylenebis(dithiocarbamate) (zinc complex) (IIa),
  manganese ethylenebis(dithiocarbamate) (IIb),
  zinc ammoniate ethylenebis(dithiocarbamate) (IIc) and
  zinc ethylenebis(dithiocarbamate) (IId); and f) an active ingredient of formula VI,

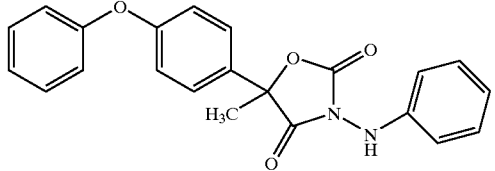

and wherein the amide compound and the at least one further active ingredient are present in synergisitcally effective amounts and in a weight ratio of from 10:1 to 1:10.

2. The composition defined in claim 1, wherein $R^4$ is chlorine and $R^{10}$ is halogen.

3. The composition defined in claim 1, wherein the amide compound is a compound of formula

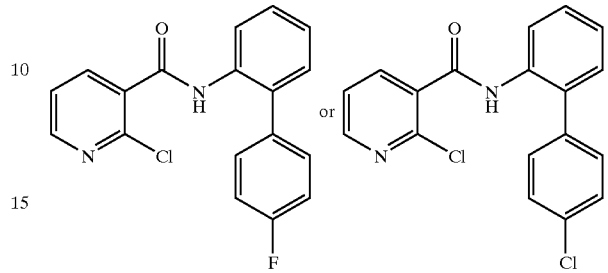

4. The composition defined in claim 1, which is conditioned in two parts, one part comprising the amide compound in a solid or liquid carrier and the other part comprising the at least one further active ingredient in a solid or liquid carrier.

5. A method for controlling harmful fungi, which comprises treating the fungi, their habitat, or materials, plants, seeds, soils, areas or spaces to be protected against fungal attack with an effective amount of the composition defined in claim 1, where the active components are applied simultaneously jointly or separately, or in succession.

6. The composition defined in claim 1, which comprises as active components
  a) the amide compound, and
  b) the dithiocarbamate (II).

7. The composition defined in claim 1, which comprises as active components
  a) the amide compound, and
  b) the dithiocarbamate (IIa).

8. The composition defined in claim 1, which comprises as active components
  a) the amide compound, and
  f) the active ingredient of formula VI.

* * * * *